(12) United States Patent
Tzeng et al.

(10) Patent No.: US 8,902,420 B2
(45) Date of Patent: Dec. 2, 2014

(54) SENSOR CHIP FOR BIOMEDICAL AND MICRO-NANO STRUCTURED SUBSTANCES AND METHOD FOR MANUFACTURING THE SAME

(75) Inventors: Yon-Hua Tzeng, Tainan (TW); Chih-Yi Liu, New Taipei (TW); Chen-Han Huang, Tainan (TW); Hsing-Ying Lin, Kaohsiung (TW); Hsiang-Chen Chui, Taichung (TW); Kyaw-Oo Lau, Tainan (TW); Shih-Tse Chen, New Taipei (TW); Cheng-Wen Huang, Kaohsiung (TW)

(73) Assignee: National Cheng Kung University, Tainan (TW)

( * ) Notice: Subject to any disclaimer, the term of this patent is extended or adjusted under 35 U.S.C. 154(b) by 266 days.

(21) Appl. No.: 13/337,340

(22) Filed: Dec. 27, 2011

(65) Prior Publication Data

US 2012/0194813 A1    Aug. 2, 2012

(30) Foreign Application Priority Data

Jan. 27, 2011 (TW) .............................. 100103085 A
Oct. 13, 2011 (TW) .............................. 100137198 A

(51) Int. Cl.
*G01J 3/44* (2006.01)
*G01N 21/65* (2006.01)

(52) U.S. Cl.
CPC .................................. *G01N 21/658* (2013.01)
USPC ...................................................... 356/301

(58) Field of Classification Search
CPC ........ G01N 21/658; B82Y 5/00; B82Y 15/00; B82Y 20/00; B82Y 30/00; B82Y 35/00; B82Y 40/00
USPC ...................... 356/301; 205/79; 977/810, 773
See application file for complete search history.

(56) References Cited

U.S. PATENT DOCUMENTS 7,453,565 B2 * 11/2008 Wang et al. .................... 356/301
7,579,588 B2 * 8/2009 Naya et al. ..................... 250/288
(Continued)

FOREIGN PATENT DOCUMENTS

CN          101832933 A     9/2010

OTHER PUBLICATIONS

Chen-Han Huang, Hsing-Ying Lin, Shihtse Chen, Chih-Yi Liu, Hsiang-Chen Chui, and Yonhua Tzeng, "Electrochemically fabricated self-aligned 2-D silver/alumina arrays as reliable SERS sensors," Optics Express, vol. 19, No. 12, Jun. 6, 2011, published May 27, 2011.*

(Continued)

*Primary Examiner* — Kara E Geisel
*Assistant Examiner* — Violetta A Prieto
(74) *Attorney, Agent, or Firm* — Bacon & Thomas, PLLC

(57) ABSTRACT

The present invention relates to a sensor chip for biomedical and micro-nano structured substances and a method for manufacturing the same. The sensor chip includes plural metal nanoparticles and a porous anodized aluminum oxide film. The plural metal nanoparticles are completely contained in holes of the porous anodized aluminum oxide film and located at the bottom of the holes, and an aluminum oxide layer covering the second end of the holes has a thickness of 1 nm to 300 nm. When analytes such as biomedical molecules are provided in contact with the sensor chip, a Raman signal can be detected based on the Raman spectroscopy. The structure of the sensor chip of the present invention is uncomplicated and the manufacturing steps thereof are simple, and therefore the sensor chip of the present invention is of great commercial value. Also, a method of manufacturing the above sensor chip is disclosed.

12 Claims, 10 Drawing Sheets

(56) References Cited

U.S. PATENT DOCUMENTS

| | | | |
|---|---|---|---|
| 8,008,620 B2* | 8/2011 | Ikeda et al. | 250/288 |
| 8,278,626 B2* | 10/2012 | Murakami et al. | 250/425 |
| 8,279,436 B2* | 10/2012 | Lin et al. | 356/301 |
| 8,461,511 B2* | 6/2013 | Tzeng et al. | 250/216 |
| 8,502,970 B2* | 8/2013 | Tomaru | 356/301 |
| 2004/0183176 A1* | 9/2004 | Naya et al. | 257/680 |
| 2005/0105085 A1* | 5/2005 | Naya | 356/301 |
| 2007/0158549 A1* | 7/2007 | Naya et al. | 250/288 |
| 2007/0165217 A1* | 7/2007 | Johansson et al. | 356/301 |
| 2007/0285657 A1* | 12/2007 | Wang et al. | 356/301 |
| 2010/0149529 A1* | 6/2010 | Biris et al. | 356/301 |
| 2012/0037792 A1* | 2/2012 | Tzeng et al. | 250/214 SW |

OTHER PUBLICATIONS

Chih-Yi Liu, Keng-Chih Liang, Waileong Chen, Chia-hao Tu,4 Chuan-Pu Liu, and Yonhua Tzeng, "Plasmonic coupling of silver nanoparticles covered by hydrogen-terminated graphene for surface-enhanced Raman spectroscopy," Optics Express, vol. 19, No. 18, Aug. 29, 2011, published Aug. 16, 2011.*

Kun-Tong Tsai, Yu-Rong Huang, Ming-Yu Lai, Chih-Yi Liu, Huai-Hsien Wang, Jr-Hau He, and Yuh-Lin Wang, "Identical-Length Nanowire Arrays in Anodic Alumina Templates," Journal of Nanoscience and Nanotechnology vol. 10, 8293-8297, 2010.*

Chen-Han Huang, Hsing-Ying Lin, Ben-Chao Lau, Chih-Yi Liu, Hsiang-Chen Chui, and Yonhua Tzeng, Plasmon-induced optical switching of electrical conductivity in porous anodic aluminum oxide films encapsulated with silver nanoparticle arrays, Optics Express, 2010, p. 27891-27899, OSA.

Chang Po, Prepration of silver nanoparticles and study of the properties of surface enhancing Raman spectrum of the same, 2010, China.

* cited by examiner ic and micro-nano structured substances and a method for manufacturing the same, more particularly, to a sensor chip including a plurality of metal nanoparticles and an anodized aluminum oxide film and a method for manufacturing the same.

SENSOR CHIP FOR BIOMEDICAL AND MICRO-NANO STRUCTURED SUBSTANCES AND METHOD FOR MANUFACTURING THE SAME

CROSS REFERENCE TO RELATED APPLICATION

This application claims the benefits of the Taiwan Patent Application Ser. No. 100103085 filed on Jan. 27, 2011 and the Taiwan Patent Application Ser. No. 100137198 filed on Oct. 13, 2011, and the subject matters of which are incorporated herein by reference.

BACKGROUND OF THE INVENTION

1. Field of the Invention

The present invention relates to a sensor chip for biomedical and micro-nano structured substances and a method for manufacturing the same, more particularly, to a sensor chip including a plurality of metal nanoparticles and an anodized aluminum oxide film and a method for manufacturing the same.

2. Description of Related Art

Sensor chips for biomedical and micro-nano structured substances can be applied in drug development, disease and physical assays, DNA sequencing and tissue processing. Sensor chips for biomedical and micro-nano structured substances preferably exhibit high sensitivity, require minimal amount of samples, allow multiple assays to be run in parallel, show rapid response, have an integrated structure and reduce assay costs. The development of sensor chips for biomedical and micro-nano structured substances is helpful to keep the quality of life for an aging society and the research of novel micro-nano materials. Typical detection techniques for biomedical and micro-nano structured substances include laser-induced fluorescence (LIF) analysis, surface plasma resonance (SPR) analysis, enzyme-linked immunosorbent assay (ELISA) and Raman spectroscopy.

Raman spectroscopy can achieve rapid detection and is involved in light scattering, interactions with electrons, and polarization. Raman spectroscopy includes surface-enhanced Raman scattering (SERS) spectroscopy, tip-enhanced Raman scattering (TERS) spectroscopy and polarized Raman scattering spectroscopy. Surface-enhanced Raman scattering (SERS) analysis is a highly sensitive method for analyzing various types of molecules adsorbed on the surface of analytes on the basis of Raman scattering signal enhancement of molecules on a metal surface. That is, the interaction between light and substances can be enhanced by surface plasmons on the substrate so as to greatly enhance Raman signal. Therefore, chips for surface-enhanced Raman scattering detection have attracted research interest.

For chips for surface-enhanced Raman scattering (SERS) measurement, it is essential to form nano-sized metal particles or a metal film with a nanostructure on a substrate (such as a glass substrate, a silicon-based substrate and so on). It is preferable to regularly arrange metal particles with uniform sizes on the substrate. The methods for forming the metal particles include, for example, evaporation, deposition and coating. However, the above-mentioned methods show poor efficiency in the adjustment of sizes, shapes and arrangement of micro- or nano-sized metal particles. In addition, the chips obtained by the above-mentioned methods suffer easy degradation due to the exposure of the metal particles in environments, and thus have difficulty in achieving stability and reusability. Accordingly, it is desirable to develop a sensor chip in a novel structure and a method for manufacturing the same to achieve the features of uniform sizes, complete shapes, regular arrangement and inhibited degradation (owing to no influence caused by environment and analytes) of metal particles, improved stability and reusability, and thus to promote the advancement of SERS applied in detection of biomedical and micro-nano structured substances.

SUMMARY OF THE INVENTION

The present invention provides a sensor chip for biomedical and micro-nano structured substances, which includes a plurality of metal nanoparticles and an anodized aluminum oxide film. Herein, the anodized aluminum oxide film is made of a porous material with nano-pores, and has a first surface and a second surface opposite to the first surface. In addition, the anodized aluminum oxide film has a plurality of long tube shaped holes. Each hole has a first end and a second end. The first end has an opening at the first surface of the anodized aluminum oxide film, while the second end of the hole is closed and located at the second surface of the anodized aluminum oxide film. The closed second end is covered by a transparent barrier layer with high electrical resistance. The plural metal nanoparticles are completely contained in the holes. The barrier layer covering the second end of the anodized aluminum oxide film has a thickness of 1 nm to 300 nm. When analytes (such as biomedical molecules) are provided in contact with the barrier layer at the second end of the sensor chip, Raman scattering signals can be detected by Raman spectroscopy analysis.

In the sensor chip for biomedical and micro-nano structured substances according to the present invention, the barrier layer covering the second end of the anodized aluminum oxide film has a thickness of 1 mu to 300 nm. Accordingly, when Raman scattering signals are detected using the sensor chip of the present invention, light for irradiating the metal nanoparticles can pass through and is not affected by the transparent barrier layer at the second surface, and plasmons generated at the metal nanoparticles due to light illumination and the enhanced electromagnetic field between adjacent metal nanoparticles would not be cut off by the barrier layer with high electrical resistance. Therefore, the sensor chip of the present invention exhibits SERS activity, and the barrier layer covering the second end of the anodized aluminum oxide film can protect the metal nanoparticles against the direct contact with analytes.

Concerning providing analytes in contact with the metal nanoparticles, some disadvantages may be found as follows. (1) The metal nanoparticles are easy to deteriorate due to, for example, oxidation or vulcanization. Hence, SERS activity may be affected, resulting in unstable signals (that is, signals may be sometimes strong and sometimes weak) or even disappearing signals when the degradation is serious. (2) The analytes may be degraded due to physical or chemical reaction between nanoparticles and the analytes. For example, the known sterilization function of silver nanoparticles may cause difficulty in detection if the analytes are bacteria. (3) It is not easy to clean and preserve the chip. After the chip is used to detect an analyte, the analyte may remain on the chip. Thus, physical or chemical cleaning is required before using the chip to detect a new analyte. However, the metal particles may be damaged or degraded in a cleaning process due to their exposure to ambient environments, resulting in a change of detecting function and difficulty in reusability. (4) It is not easy to preserve the chip. If the chip is unused for long time and is exposed to air, the chip may become contaminated.

The barrier layer covering the second surface of the aluminum oxide film provides benefits to the sensor chip of the present invention as follows. A light can illuminate the metal nanoparticles through the barrier layer and would not be blocked. Meanwhile, the plasmons generated at the metal nanoparticles due to light irradiation and the enhanced electromagnetic field between adjacent metal nanoparticles would not be cut off by the dielectric aluminum oxide. Accordingly, the analyte adsorbed on the barrier layer can be efficiently excited to induce enhanced Raman signal.

The barrier layer in the sensor chip of the present invention can resolve many disadvantages. For example, (1) the barrier layer can provide protection to metal nanop articles against contact with ambient environments or analytes and thus against degradation, resulting in stable signals; (2) the degradation of analytes can be avoided due to not being in direct contact with metal nanoparticles; and (3) SERS activity of the sensor chip is contributed to the metal particles rather than the covering layer, and thus the detection function of the sensor chip would not be affected on condition that the metal nanoparticles are not damaged even if the barrier layer is slightly damaged or degraded: In addition, since only the barrier layer (or other layers covering the barrier layer) is in contact with ambient environments or analytes, cleaning is required for the barrier layer (or other layers covering the barrier layer) only but not the metal particles. Accordingly, the metal nanoparticles can be protected from degradation.

In the sensor chip of the present invention, the material of the protective barrier layer covering the second end of the nano-pores preferably is a transparent dielectric material with high electrical resistance, such as silicon dioxide, zinc oxide, aluminum oxide or graphene with hydrogen or fluorine atoms attached on one or both surfaces thereof, and more preferably is consistent with the above-mentioned porous material with nano-pores, such as aluminum oxide bather layer which has a thickness controllable by process parameters and covers the second surface of the anodized aluminum oxide film.

In the sensor chip of the present invention, the thickness of the barrier layer covering the second end of the anodized aluminum oxide film can range from 1 nm to 300 nm, preferably from 1 nm to 60 nm, more preferably from 1 nm to 10 nm, and most preferably from 2 nm to 4 nm. The sensor chip of the present invention preferably further includes a functional film or an attachment, which covers the second surface (i.e. completely or partially covers the barrier layer), such that the adhesion of the analyte onto the sensor chip can be enhanced by providing the analyte in contact with the functional film, resulting in enhanced intensity of signal. For example, an antibody against specific bacteria, completely or partially covering the barrier layer, can enhance the adhesion of the specific bacteria and inhibit the adhesion of other biomedical molecules and bacteria on the sensor chip, resulting in the enhanced intensity of signals. Moreover, the adhesion of specific analytes can be selectively enhanced while inhibiting the adhesion of other impurities, so as to provide better detection for the analyte and to improve the signal-to-noise ratio.

The sensor chip of the present invention preferably further includes a passivation layer (such as a silicon oxide layer), which covers the first surface of the anodized aluminum oxide film. The passivation layer can seal the holes with the metal nanoparticles encapsulated therein and protects the metal nanoparticles from being oxidized and degraded due to contact with ambient air and moisture, so as to enhance the preservation stability of the sensor chip.

In the sensor chip of the present invention, the barrier layer covering the second end of the anodized aluminum oxide film can have a thickness of 1 nm to 300 nm, preferably 1 nm to 60 nm, more preferably 1 nm to 10 nm, and most preferably 2 nm to 4 nm.

In the sensor chip of the present invention, the Raman spectroscopy analysis preferably is surface-enhanced Raman scattering (SERB) analysis.

In the sensor chip of the present invention, the opening diameter of the hole preferably ranges from 10 nm to 400 nm, and more preferably from 25 nm to 400 nm.

In the sensor chip of the present invention, the metal nanop articles preferably have a diameter of 10 nm to 400 nm, and more preferably 25 nm to 400 nm, in a direction parallel to the second surface of the anodized aluminum oxide layer.

In the sensor chip of the present invention, the metal nanoparticles may be solid or hollow, and may have columnar, quasi-spherical, elliptical or irregular shapes. The material of the metal nanoparticles preferably is selected from the group consisting of silver, gold, copper, nickel, chromium, tungsten, platinum, aluminum and an alloy thereof, and more preferably is silver.

The sensor chip of the present invention preferably further includes a passivation layer disposed over the first surface of the anodized aluminum oxide film. The passivation layer can seal the hole to protect the metal nanoparticles from being oxidized or to prevent the entrance of moisture or impurities. The passivation layer can be made of an encapsulating material that has water-, air leakage- and corrosion-proof properties and is chemically inert with respect to environments. Preferably, the passivation layer is made of a transparent encapsulating material, such as glass or silicon oxide.

The present invention further provides a method for manufacturing a sensor chip, which includes: (A) providing an aluminum plate; (B) performing an anodizing treatment on the aluminum plate to form an anodized aluminum oxide film on a surface of the aluminum plate, in which the anodized aluminum oxide film is made of a porous material with nano-pores and has a first surface, a second surface opposite to the first surface and a plurality of long tube shaped holes, and each of the holes has a first end and a second end, therewith the first end having an opening at the first surface of the anodized aluminum oxide film, the second end of the hole being closed and located at the second surface of the anodized aluminum oxide film, and the closed second end being covered by an aluminum oxide layer; (C) growing metal nanoparticles in the holes of the anodized aluminum oxide film to make the metal nanoparticles completely contained in the holes and in touch with the bottom of the holes; (D) removing the non-oxidized aluminum plate; and (E) thinning the aluminum oxide layer covering the second end of the anodized aluminum oxide film to a thickness of 1 nm to 300 nm (preferably 1 nm to 60 nm, more preferably 1 nm to 10 nm, most preferably 2 nm to 4 nm). Accordingly, the sensor chip is obtained.

In the sensor chip manufactured by the present invention, the aluminum oxide layer covering the second end of the anodized aluminum oxide film has a thickness of 1 nm to 300 nm, preferably 1 nm to 60 nm, more preferably 1 nm to 10 nm and most preferably 2 nm to 4 nm. Hence, in the case of using the sensor chip, it is preferable to provide analytes in contact with the second surface of the anodized aluminum oxide film and to provide light exposure to the aluminum oxide layer. That is, when the sensor chip manufactured by the present invention is used to determine Raman scattering signals, the light can illuminate the metal nanoparticles through the aluminum oxide layer and would not be affected. Meanwhile, the plasmons generated at the metal nanoparticles due to light irradiation and the enhanced electromagnetic field between adjacent metal nanoparticles would not be cut off by the aluminum oxide layer. Accordingly, the sensor chip of the present invention exhibits SERS activity, and the metal nanoparticles can be protected from direct contact with the analyte.

In the method for manufacturing the sensor chip according to the present invention, preferably, the aluminum oxide layer is thinned in the step (E) by etching the aluminum oxide layer with a solution (such as 5% phosphoric acid solution) or other chemical methods, or by chemical-mechanical polishing, or by physical grinding such as ion beam milling or sputtering.

In the method for manufacturing the sensor chip according to the present invention, when an analyte is in contact with the sensor chip, it is preferable to determine Raman scattering signals by Raman spectroscopy analysis.

In the method for manufacturing the sensor chip according to the present invention, the metal nanoparticles preferably are formed by electrodeposition or other plating ways in the step (C).

In the method for manufacturing the sensor chip according to the present invention, the aluminum oxide layer covering the second end of the anodized aluminum oxide film in the step (E) preferably has a thickness of 1 nm to 300 nm, more preferably 1 nm to 60 nm, much more preferably 1 nm to 10 nm and most preferably 2 nm to 4 nm.

Preferably, the method for manufacturing the sensor chip according to the present invention further includes a step (B1) after the step (B): placing the anodized aluminum film into an etching solution to enlarge the opening diameter of the hole. Herein, examples of the etching solution may include phosphoric acid aqueous solution or other acid solution.

Preferably, the method for manufacturing the sensor chip according to the present invention further includes a step (F) after the step (E): forming a passivation layer over the first surface of the anodized aluminum oxide film. The passivation layer can protect the metal nanoparticles in the holes from being oxidized or prevent the entrance of moisture or impurities. The passivation layer can be made of an encapsulating material that has water-, air leakage- and corrosion-proof properties and is chemically inert with respect to environments. Preferably, the passivation layer is made of a transparent encapsulating material, such as glass or silicon oxide.

In the method for manufacturing the sensor chip according to the present invention, the opening diameter of the hole in the step (B) preferably ranges from 10 nm to 400 nm and more preferably from 25 nm to 400 nm.

In the method for manufacturing the sensor chip according to the present invention, the material of the metal nanoparticles preferably is selected from the group consisting of silver, gold, copper, nickel, chromium, tungsten, platinum, aluminum and an alloy thereof, and more preferably is silver.

In the method for manufacturing the sensor chip according to the present invention, the metal nanoparticles may be solid or hollow, and may have columnar, quasi-spherical, elliptical or irregular shapes.

The present invention further provides a method for manufacturing a sensor chip, which includes: (A) providing an aluminum plate; (B) performing an anodizing treatment on the aluminum plate to form an anodized aluminum oxide film on a surface of the aluminum plate, in which the anodized aluminum oxide film is made of a porous material with nano-pores and has a first surface, a second surface opposite to the first surface and a plurality of long tube shaped holes, and each of the holes has a first end and a second end, therewith the first end having an opening at the first surface of the anodized aluminum oxide film, the second end of the hole being closed and located at the second surface of the anodized aluminum oxide film, and the closed second end being covered by an aluminum oxide layer; (C) growing metal nanoparticles in the holes of the anodized aluminum oxide film to make the metal nanoparticles completely contained in the holes; (D) removing the aluminum plate; (E) removing the aluminum oxide layer covering the second end of the anodized aluminum oxide film to expose the metal nanoparticles; and (F) forming a barrier layer in a thickness of 1 nm to 300 nm such that the barrier layer covers the second end of the anodized aluminum oxide film and the metal nanoparticles. Accordingly, the sensor chip is obtained.

In the sensor chip manufactured by the present invention, the barrier layer covering the second end of the anodized aluminum oxide film has a thickness of 1 nm to 300 nm, preferably 1 nm to 60 nm, more preferably 1 nm to 10 nm and most preferably 2 nm to 4 nm. Hence, in the case of using the sensor chip, it is preferable to provide analytes in contact with the barrier layer and to provide light exposure to the barrier layer. That is, when the sensor chip manufactured by the present invention is used to determine Raman scattering signals, the light can illuminate the metal nanoparticles through the barrier layer and would not be affected. Meanwhile, the plasmons generated at the metal nanoparticles due to light irradiation and the enhanced electromagnetic field between adjacent metal nanoparticles would not be cut off by the barrier layer. Accordingly, the sensor chip of the present invention exhibits SERS activity, and the metal nanoparticles can be protected from direct contact with the analyte.

In the method for manufacturing the sensor chip according to the present invention, preferably, the aluminum oxide layer is thinned in the step (E) by etching the aluminum oxide layer with an acid solution or by physical methods.

In the method for manufacturing the sensor chip according to the present invention, preferably, the barrier layer is formed by, for example, ion beam sputtering, physical vapor deposition, chemical vapor deposition or atomic layer deposition, or by overlaying the second end with a pre-synthesized transparent film having high electrical resistance in the step (F).

In the method for manufacturing the sensor chip according to the present invention, when an analyte is in contact with the barrier layer of the sensor chip, it is preferable to determine Raman scattering signals by Raman spectroscopy analysis.

In the method for manufacturing the sensor chip according to the present invention, the metal nanoparticles preferably are formed by electrodeposition or other plating ways in the step (C).

The method for manufacturing the sensor chip according to the present invention can further include a step (B1) after the step (B): placing the anodized aluminum film into an etching solution to enlarge the opening diameter of the hole.

In the method for manufacturing the sensor chip according to the present invention, the opening diameter of the hole in the step (B) preferably ranges from 10 nm to 400 nm and more preferably from 25 nm to 400 nm.

In the method for manufacturing the sensor chip according to the present invention, the material of the metal nanoparticles preferably is selected from the group consisting of silver, gold, copper, nickel, chromium, tungsten, platinum, aluminum and an alloy thereof.

In the method for manufacturing the sensor chip according to the present invention, the material of the barrier layer preferably is a transparent dielectric material with high electrical resistance, such as silicon dioxide, zinc oxide, aluminum oxide or graphene with hydrogen or fluorine atoms attached on one or both surfaces thereof, and more preferably is consistent with the above-mentioned porous material with nano-pores, such as aluminum oxide.

In the method for manufacturing the sensor chip according to the present invention, the barrier layer preferably has a thickness of 1 nm to 60 nm, more preferably 1 nm to 10 nm and most preferably 2 nm to 4 nm.

In the method for manufacturing the sensor chip according to the present invention, the metal nanoparticles may be solid or hollow, and may have columnar, quasi-spherical, elliptical or irregular shapes.

Preferably, the method for manufacturing the sensor chip according to the present invention further includes a step (G) after the step (F): forming a passivation layer over the first surface of the anodized aluminum oxide film.

BRIEF DESCRIPTION OF THE DRAWINGS

FIGS. 4E' to 4F' show a process for manufacturing a sensor chip according to Example 5 of the present invention;

DETAILED DESCRIPTION OF THE PREFERRED EMBODIMENT

Example 1

Figure 1A:
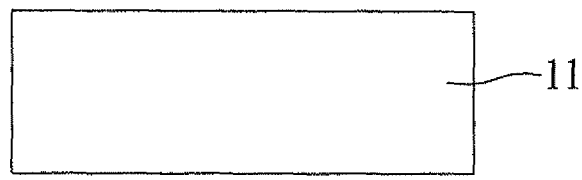
FIGS. 1A to 1E show a process for manufacturing a sensor chip according to Example 1 of the present invention.
Figure 1B:
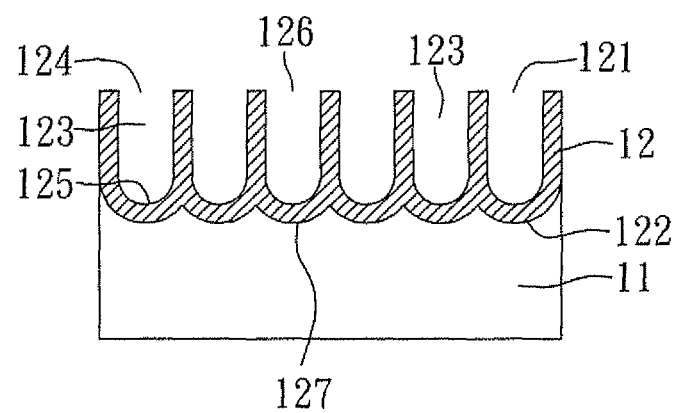
Figure 1C:
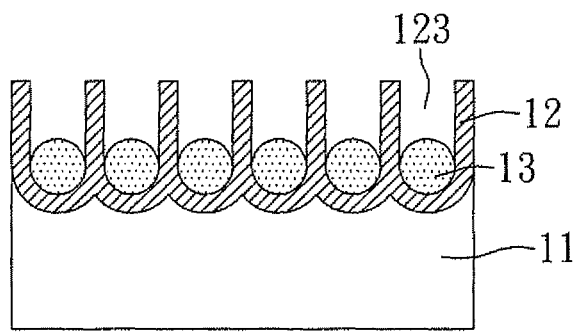
Figure 1D:
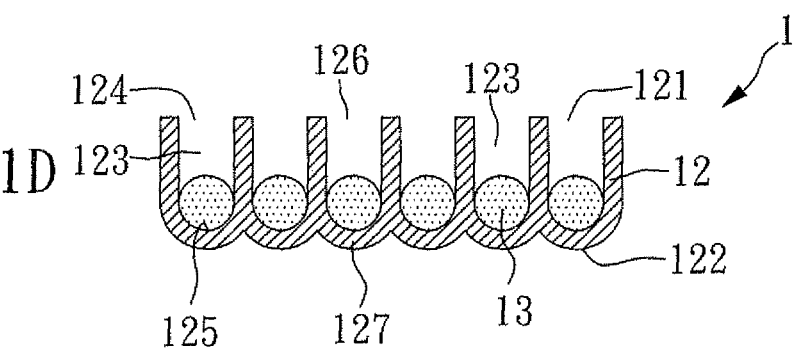
Figure 1E:
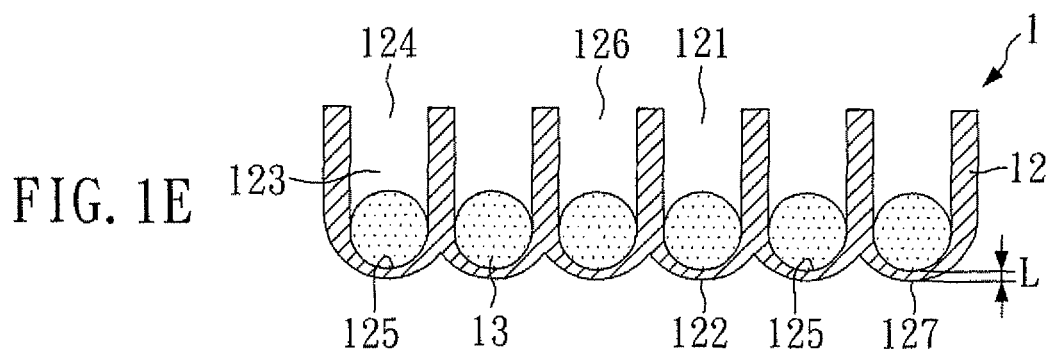

FIGS. 1A to 1E show a process to manufacture a sensor chip according to the present example. As shown in FIG. 1A, an aluminum plate 11 is first provided in the step (A). Then, as shown in FIG. 1B, the aluminum plate 11 is subjected to an anodizing treatment to form an aluminum oxide film 12 on the surface of the aluminum plate 11 in the step (B). The film 12 is made of a porous material with nano-pores, and has a first surface 121 and a second surface 122 opposite to the first surface 121. In addition, the anodized aluminum oxide film 12 has a plurality of long tube shaped holes 123. Each of the holes 123 has a first end 124 and a second end 125. The first end 124 has an opening 126 at the first surface 121 of the anodized aluminum oxide film 12, while the second end 125 of the hole 123 is closed and located at the second surface 122 of the anodized aluminum oxide film 12. The closed second end 125 is covered by an aluminum oxide layer 127. Subsequently, as shown in FIG. 1C, through electrodeposition, silver nanoparticles 13 are grown and completely contained in the holes 123 of the anodized aluminum oxide film 12 under an alternating current of 15 V in the step (C). Then, as shown in FIG. 1D, the aluminum plate 11 is removed by an etching process in the step (D). Finally, as shown in FIG. 1E, the aluminum oxide layer 127 covering the second end 125 of the anodized aluminum oxide film 12 is thinned by making the aluminum oxide layer 127 contact with 5% phosphoric acid solution in the step (E), until the aluminum oxide layer 127 covering the second end 125 of the anodized aluminum oxide film 12 has a thickness L of, for example, 30 nm. A thinner aluminum oxide layer 127 is more preferable. Accordingly, the sensor chip 1 is obtained.

Figure 2:
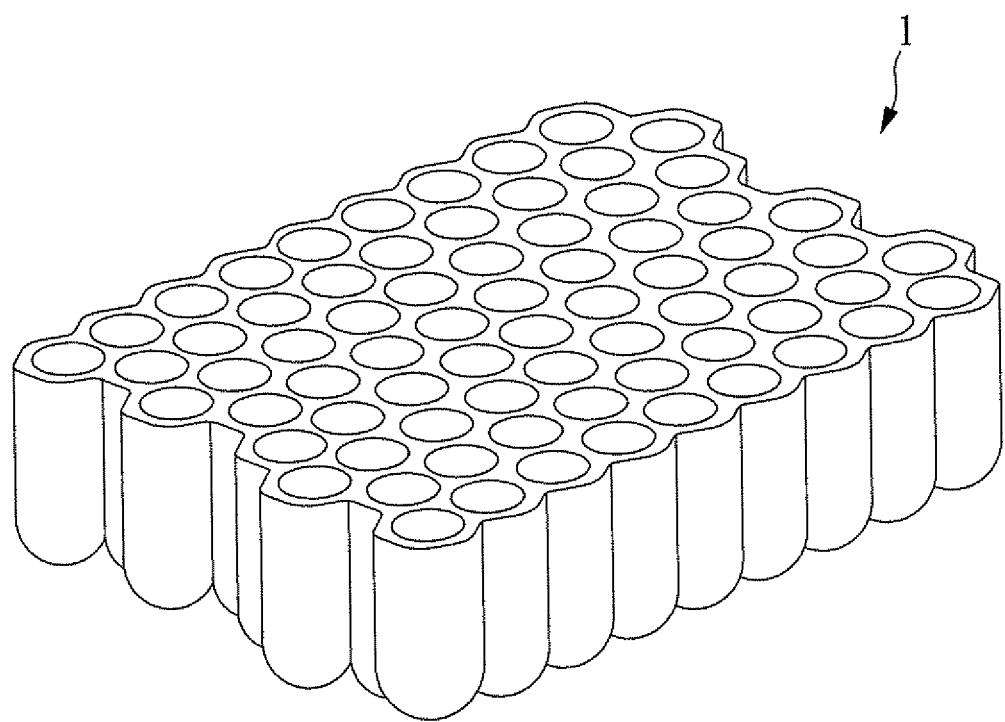
FIG. 2 shows a perspective view of a sensor chip according to Example 1 of the present invention.

FIGS. 1E and 2 show a sensor chip 1 manufactured by the present example. The sensor chip 1 according to the present example includes a plurality of silver nanoparticles 13 and an anodized aluminum oxide film 12. The anodized aluminum oxide film 12 is made of a porous material with nano-pores, and has a first surface 121 and a second surface 122 opposite to the first surface 121. In addition, the anodized aluminum oxide film 12 has a plurality of long tube shaped holes 123. Each of the holes 123 has a first end 124 and a second end 125. The first end 124 has an opening 126 at the first surface 121 of the anodized aluminum oxide film 12, while the second end 125 of the hole 123 is closed and located at the second surface 122 of the anodized aluminum oxide film 12. The closed second end 125 is covered by an aluminum oxide layer 127, and the plural silver nanoparticles 13 are completely encapsulated in the holes 123 and in touch with the bottom of the holes 123. The aluminum oxide layer 127 covering the second end 125 of the anodized aluminum oxide film 12 has a thickness L of 30 nm.

Figure 3A:
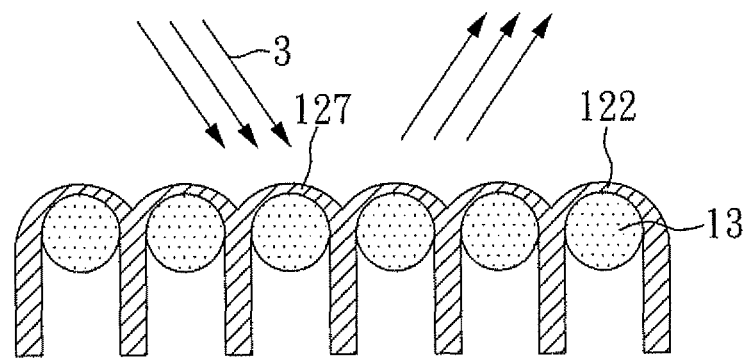
FIGS. 3A and 3B show a perspective view of a sensor chip according to Example 1 of the present invention.

As shown in FIG. 3A, in the case of using the sensor chip 1 of the present example to detect Raman scattering signals, an analyte containing molecules to be analyzed (not shown in the figure) is provided in contact with the aluminum oxide layer 127, and the second surface 122 of the aluminum oxide layer 127 is irradiated by light 3. Accordingly, the metal nanoparticles 13 would be irradiated by the light 3, which can pass through and is not blocked by the aluminum oxide layer 127, and thus SERS signal is detected. The anodized aluminum oxide exhibits good light transmittance. When the passivation layer 15 covering the first surface is made of a transparent material, the light 3 also can be directed on the first surface 121 and Raman scattering signal can be collected at the first surface or the second surface. Hence, the analyte can be provided without contacting metal nanoparticles on condition that SERS signal can be detected by the sensor chip of the present invention. The sensor chip of the present invention has advantages of stable metal nanoparticles, reusability, signal stability and easy preservation, and thus is superior to conventional sensor chips.

Figure 3B:
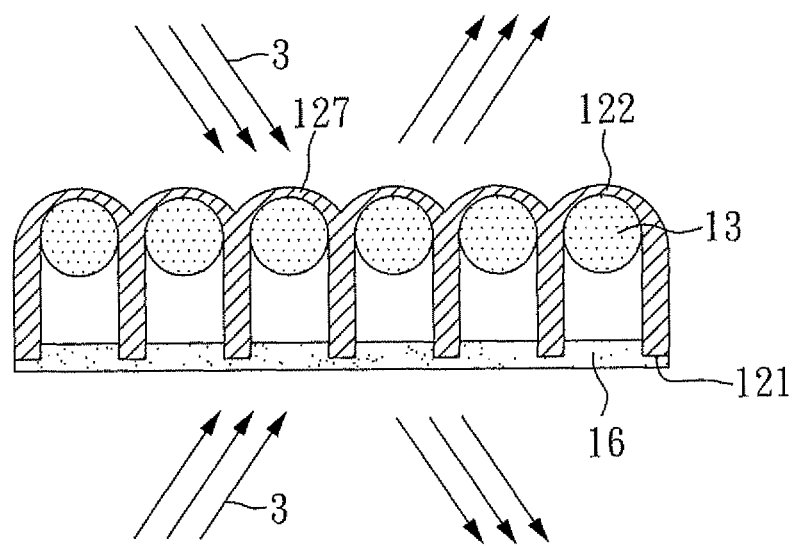

In addition, as shown in FIG. 3B, a light transparent layer 16, which may be made of, for example, silicon oxide, can be further formed at the first surface 121 to prevent dust from falling therein and protect metal nanoparticles from being oxidized. In detecting Raman scattering signal, both the upper and lower surfaces can be subjected to signal detection and light illumination. That is, both the first surface 121 and the second surface 122 can be subjected to signal detection and light illumination.

Example 2

Figure 1F:
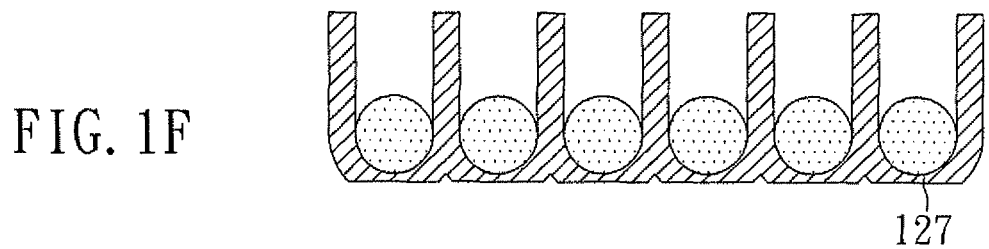
FIG. 1F shows a perspective view of a thinned sensor chip according to Example 2 of the present invention.

The sensor chip of the present example is manufactured by the same method as illustrated in Example 1, except that the present example uses a physical method (e.g. grinding) to thin the aluminum oxide layer 127 in the step (E), as shown in FIG. 1F.

In the present example, since no acid reagents are used in the physical method for thinning the aluminum oxide layer 127, the environmental pollution can be reduced. Besides, in the present example, rinsing and drying steps are unnecessary and the method is simpler.

Example 3

Figure 1G:
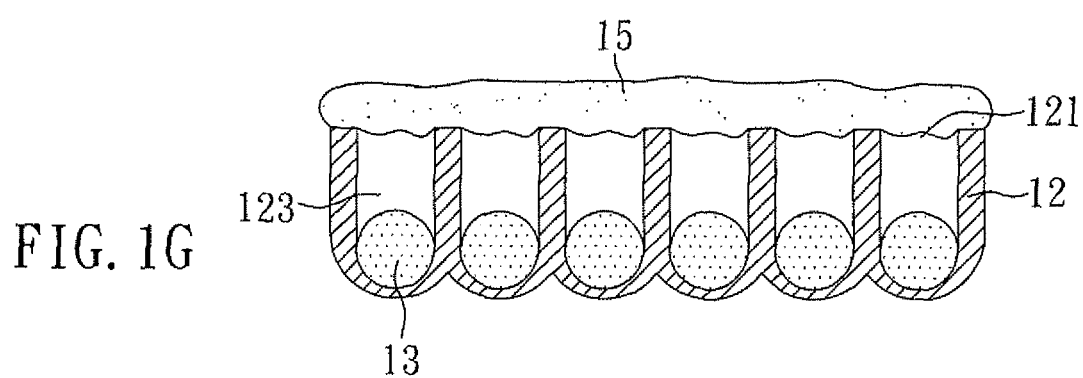
FIG. 1G shows a perspective view of a sensor chip with a passivation layer according to Example 3 of the present invention.

After the sensor chip 1 shown in FIG. 1E according to Example 1 is manufactured, a step (F) of forming a passivation layer 15, which may be made of, for example, silicon oxide, on the first surface 121 of the anodized aluminum oxide film 12 is performed, as shown in FIG. 1G. The passivation layer 15 can protect the metal nanoparticles 13 in the holes 123 from being oxidized or prevent the entrance of moisture and impurities.

Example 4

Figure 4A:
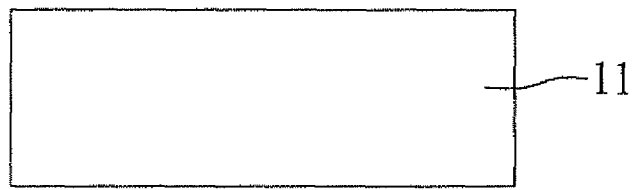
FIGS. 4A to 4G show a process for manufacturing a sensor chip according to Example 4 of the present invention.
Figure 4B:
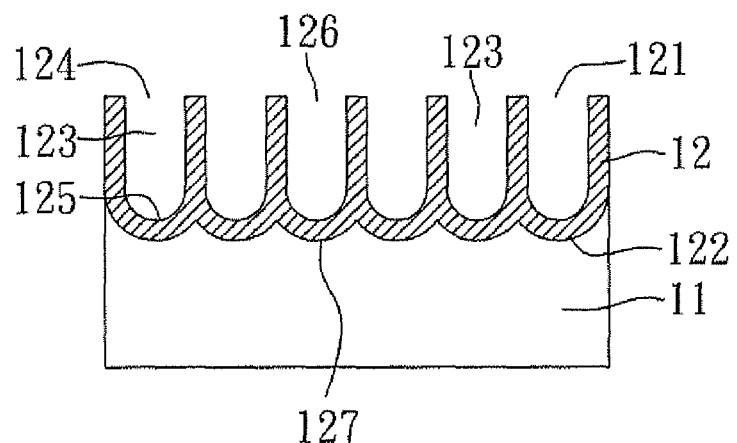
Figure 4C:
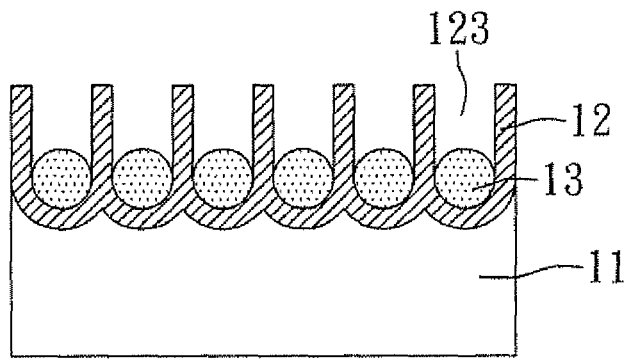
Figure 4D:
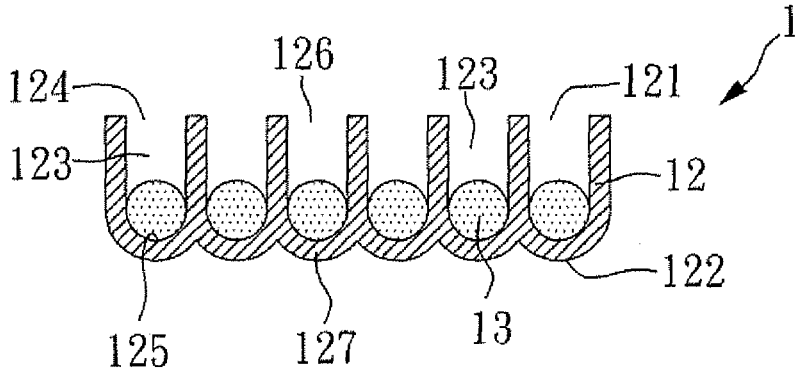

FIGS. 4A to 4E show a process to manufacture a sensor chip according to the present example. As shown in FIG. 4A, an aluminum plate 11 is first provided in the step (A). Then, as shown in FIG. 4B, the aluminum plate 11 is subjected to an anodizing treatment to form an aluminum oxide film 12 on the surface of the aluminum plate 11 in the step (B). The film 12 is made of a porous material with nano-pores, and has a first surface 121 and a second surface 122 opposite to the first surface 121. In addition, the anodized aluminum oxide film 12 has a plurality of long tube shaped holes 123. Each of the holes 123 has a first end 124 and a second end 125. The first end 124 has an opening 126 at the first surface 121 of the anodized aluminum oxide film 12, while the second end 125 of the hole 123 is closed and located at the second surface 122 of the anodized aluminum oxide film 12. The closed second end 125 is covered by an aluminum oxide layer 127. Subsequently, as shown in FIG. 4C, through electrodeposition, silver nanoparticles 13 are grown and completely contained in the holes 123 and in touch with the bottom of the holes 123 under an alternating current of 15 V in the step (C). Then, as shown in FIG. 4D, the aluminum plate 11 is removed by an etching process in the step (D).

Figure 4E:
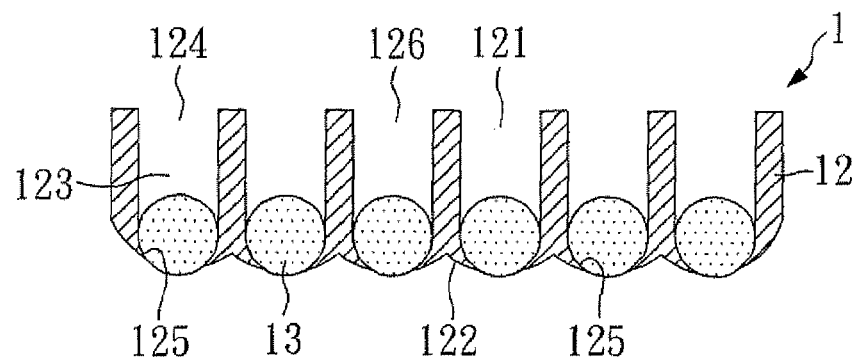

Subsequently, as shown in FIG. 4E, the aluminum oxide layer 127 covering the second end 125 of the anodized aluminum oxide film 12 is removed by making the aluminum oxide layer 127 contact with 5% phosphoric acid solution in the step (E) to expose the silver nanoparticles 13 contained in the holes 123.

Figure 4F:
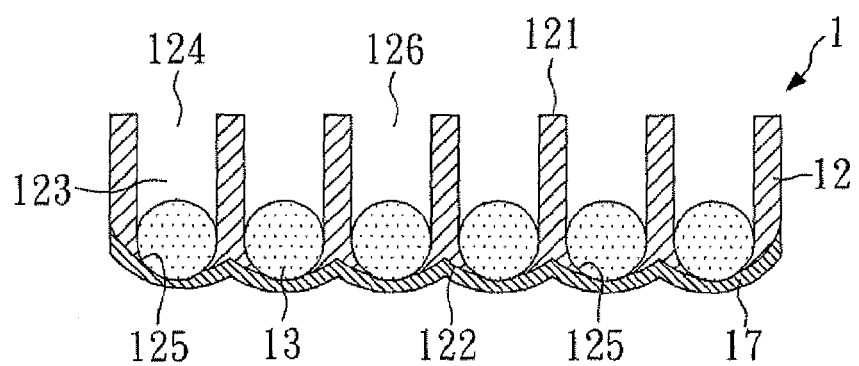

Finally, as shown in FIG. 4F, a barrier layer 17 of aluminum oxide is formed on the second surface 122 of the anodized aluminum oxide film 12 in a thickness of about 1 nm to 10 nm by a physical method, ion beam sputter deposition, such that the barrier layer 17 covers the second end 125 of the holes 123. That is, the barrier layer 17 covers the silver nanoparticles 13. As a result, the sensor chip 1 of the present example is obtained.

In the present example, the barrier layer 17 also can be formed by transferring a pre-synthesized thin film such as hydrogenated graphene or formed by chemical methods (such as atomic layer deposition), physical vapor deposition or chemical vapor deposition, but the method is not limited thereto. The thickness of the barrier layer 17 can be, for example, 1 nm, 10 nm, 30 nm, 60 nm, 200 nm or 300 nm. Its thickness can be adjusted in consideration of requirements and sensing effect.

Figure 4G:
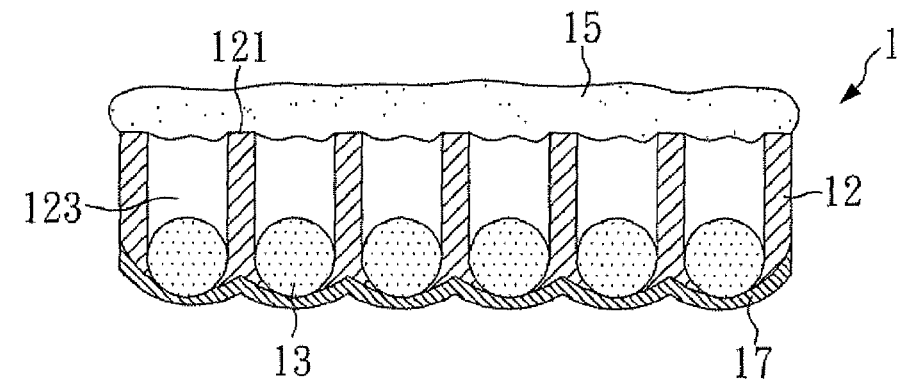
Figure 4E:
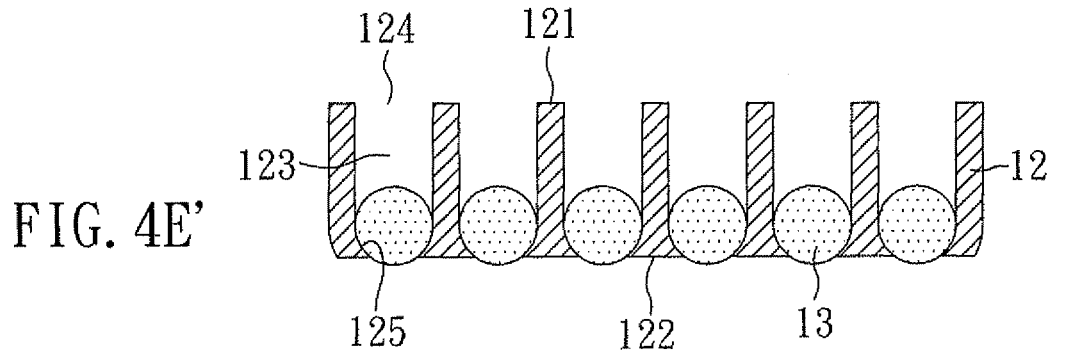
Figure 4F:
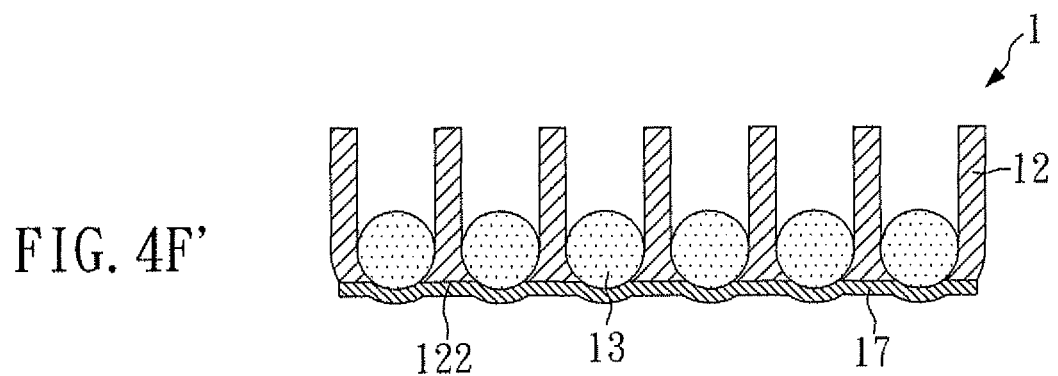

The present example may perform a step (G) after the step (F): forming a passivation layer 15 on the first surface 121 of the anodized aluminum oxide film 12, as shown in FIG. 4G.

Example 5

The sensor chip of the present example is manufactured by the same method as illustrated in Example 4, except that the present example uses a physical method (e.g. grinding) to remove the aluminum oxide layer 127 in the step (E), as shown in FIG. 4E', followed by forming a barrier layer 17 of aluminum oxide by atomic layer deposition, as shown in FIG. 4F'.

In the present example, since no acid reagents are used in the physical method for removing the aluminum oxide layer 127, the environmental pollution can be reduced. Besides, in the present example, rinsing and drying steps are unnecessary and the method is simpler.

Test Example 1

Figure 5:
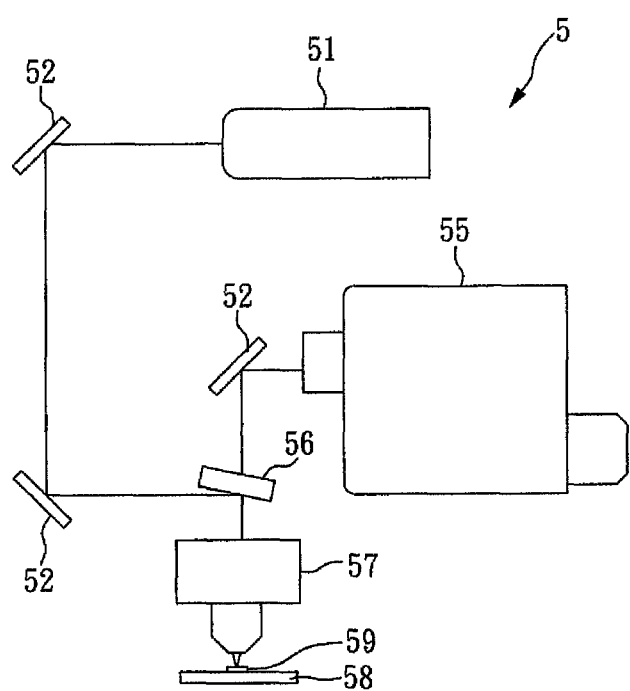
FIG. 5 shows a Raman spectroscopy system according to Test Examples of the present invention.

As shown in FIG. 5, a Raman spectroscopy system 5 is used to determine the SERS activity of the sensor chip. The system 5 includes: a He/Ne laser 51, plural optical reflective mirrors 52, a notch filter 56, a Raman spectrometer 55, a microlens 57 and a platform 58. The sensor chip 59 is placed on the platform 58 and then tested.

Rhodamine 6G (R6G, a kind of dye molecule) solution is dropped on the aluminum oxide layer of three different chips as an analyte. The three chips used in the test example are (a) an aluminum oxide (AAO) film without being embedded with Ag nanoparticles in the holes; (b) an aluminum oxide (AAO) film being embedded with Ag nanoparticles in the holes and having an unthinned aluminum oxide layer, and (c) an aluminum oxide (AAO) film being embedded with Ag nanoparticles in the holes and having a thinned aluminum oxide layer that is etched in 5% phosphoric acid for 10 minutes to reduce the distance between the metal nanoparticles and the analyte at the other side of the aluminum oxide layer and thus to enhance the intensity of the electromagnetic field generated by light excitation on the metal nanoparticles and applied to the analyte (i.e. the sensor chip according to Example 1 of the present invention).

Figure 6:
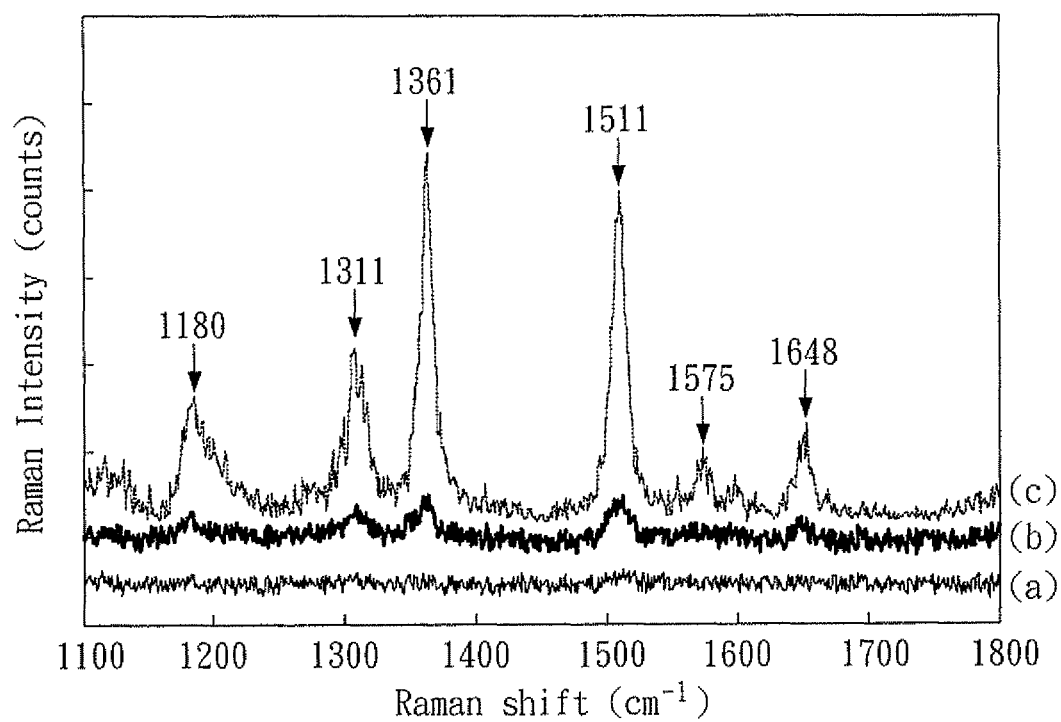
FIG. 6 shows SERS spectra according to Test Example 1 of the present invention.

This test example uses R6G as an analyte for the three chips. The R60 solution of 1 μM is provided in contact with the chip for 10 minutes, followed by rinsing the chip with deionized water. The SERS signal of the molecules is determined, as shown in Raman spectra (a), (b) and (c) of FIG. 6. FIG. 6 shows that the chip (a) indicates no detectable Raman signals; the chip (b) indicates weak Raman peak of R6G; and the chip (c) indicates strong and clear Raman peak of R6G Thus, it can be confirmed that the chip (c) (i.e. the sensor chip of the present invention) exhibits good Raman activity.

Test Example 2

As mentioned in Test Example 1, this test example uses three chips for Raman spectroscopy analysis. The three chips are (a) an aluminum oxide (AAO) film without being embedded with Ag nanoparticles in the holes; (b) an aluminum oxide (AAO) film being embedded with Ag nanoparticles in the holes and having an unthinned aluminum oxide layer, and (c) an aluminum oxide (AAO) film being embedded with Ag nanoparticles in the holes and having a thinned aluminum oxide layer that is etched in 5% phosphoric acid for 10 minutes. However, this test example uses 0.1 mM adenine as an analyte. The adenine solution of 0.1 mM is provided in contact with the chip for 30 minutes adsorption, followed by rinsing the chip with deionized water. The SERS signal of the molecules is determined, as shown in FIG. 7.

Figure 7:
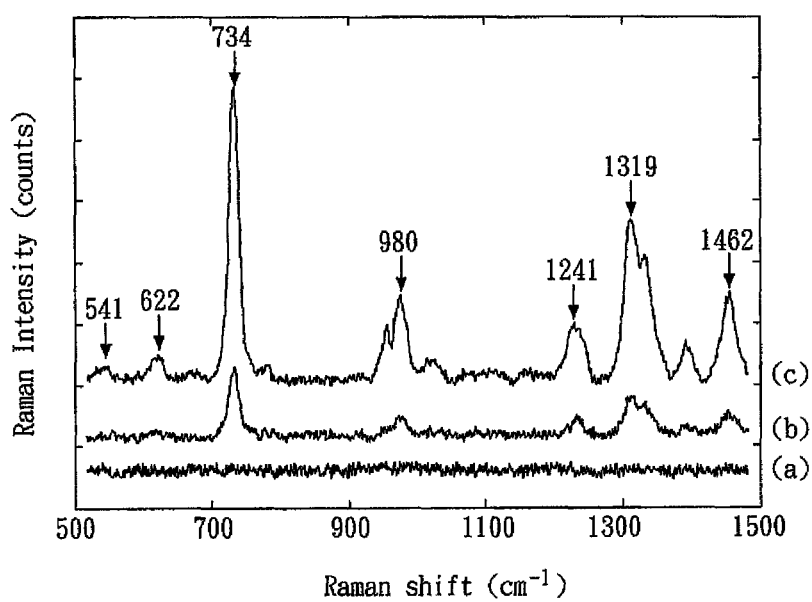
FIG. 7 shows SERS spectra according to Test Example 2 of the present invention.

FIG. 7 shows that the chip (a) indicates no detectable Raman signals; the chip (b) indicates weak Raman peak of adenine; and the chip (c) indicates strong and clear Raman peak of adenine. Thus, it can be recognized that the chip (c) (i.e. the sensor chip of the present invention) exhibits good Raman activity.

Different molecules, substances and structures have their unique Raman spectra. Thus, the sensor chip of the present invention can be used to efficiently and rapidly discriminate minute and barely detectable substances and structures, including biomedical molecules, and to function as a biosensor chip or sensor chip for other substances.

According to the sensor chip of the present invention, the barrier layer covering the second end of the anodized aluminum oxide film has a thickness of about 1 nm to 300 nm (preferably 1 nm to 60 nm, more preferably 1 nm to 10 nm, most preferably 2 nm to 4 nm). Thus, when the sensor chip of the present invention is used to determine Raman scattering signals, light can illuminate metal nanoparticles through the bather layer at the second surface and would not be blocked. Meanwhile, plasmons generated at the metal nanoparticles due to light irradiation and the enhanced electromagnetic field between adjacent metal nanoparticles would not be cut off by the barrier layer. Accordingly, the sensor chip of the present invention exhibits SERS activity, and the metal nanoparticles can be protected against direct contact with analytes.

In the sensor chip of the present invention, the barrier layer can resolve many drawbacks. For example, (1) the covering layer (i.e. the barrier layer) can provide protection to metal nanoparticles against contact with ambient environments or analytes and thus against degradation, resulting in stable signals; (2) the degradation of analytes can be avoided due to not being in direct contact with metal nanoparticles; and (3) the detection function of the sensor chip would not be affected on condition that the metal nanoparticles are free of damage even if the aluminum oxide layer is slightly damaged or degraded owing to the fact that SERS activity of the sensor chip is contributed to the metal particles rather than the covering layer. In addition, since only the barrier layer (or other layers covering the barrier layer) would be in contact with ambient environments or analytes, cleaning is required for the barrier layer (or other layers covering the barrier layer) only, but not the metal particles. Accordingly, the degradation of the metal nanoparticles can be prevented.

The above examples are intended for illustrating the embodiments of the subject invention and the technical features thereof, but not for restricting the scope of protection of the subject invention. The scope of the subject invention is based on the claims as appended.

What is claimed is:

1. A sensor chip for biomedical and micro-nano structured substances, comprising a plurality of metal nanoparticles and an anodized aluminum oxide film, wherein
the anodized aluminum oxide film is made of a porous material with nano-pores and has a first surface, a second surface opposite to the first surface and a plurality of long tube shaped holes, therewith each of the holes having a first end and a second end, the first end having an opening at the first surface of the anodized aluminum oxide film, the second end of the hole being closed and located at the second surface of the anodized aluminum oxide film, the closed second end being covered by a barrier layer, and the plural metal nanoparticles being completely contained in the holes;
the barrier layer covering the second end of the anodized aluminum oxide film has a thickness of 1 nm to 300 nm; and
a Raman signal is detectable by Raman spectroscopy analysis when an analyte is provided in contact with the barrier layer at a second end of the sensor chip.

2. The sensor chip as claimed in claim 1, wherein the barrier layer covering the second end of the anodized aluminum oxide film has a thickness of 1 nm to 60 nm.

3. The sensor chip as claimed in claim 1, wherein the barrier layer covering the second end of the anodized aluminum oxide film has a thickness of 1 nm to 10 nm.

4. The sensor chip as claimed in claim 1, wherein the barrier layer is made of silicon dioxide, zinc oxide, aluminum oxide or graphene with hydrogen or fluorine atoms attached on one or both surfaces thereof.

5. The sensor chip as claimed in claim 1, wherein the analyte is provided in contact with the second surface of the anodized aluminum oxide film of the sensor chip.

6. The sensor chip as claimed in claim 1, further comprising: a functional film or an attachment covering the second surface, wherein the analyte is provided in contact with the functional film or the attachment.

7. The sensor chip as claimed in claim 1, wherein the Raman spectroscopy analysis is surface-enhanced Raman scattering (SERS) analysis.

8. The sensor chip as claimed in claim 1, wherein the opening of the hole ranges from 10 nm to 400 nm in diameter.

9. The sensor chip as claimed in claim 1, wherein the metal nanoparticles range from 10 nm to 400 nm in diameter.

10. The sensor chip as claimed in claim 1, wherein the metal nanoparticles are made of a material selected from the group consisting of silver, gold, copper, nickel, chromium, tungsten, platinum, aluminum and an alloy thereof.

11. The sensor chip as claimed in claim 1, wherein the metal nanoparticles are solid or hollow and have columnar, quasi-spherical, elliptical or irregular shapes.

12. The sensor chip as claimed in claim 1, further comprising: a passivation layer disposed over the first surface of the anodized aluminum oxide film.

* * * * *